(12) United States Patent
Lee et al.

(10) Patent No.: US 11,097,056 B2
(45) Date of Patent: Aug. 24, 2021

(54) AUTOMATIC JET INJECTOR FOR ADMINISTERING TISSUE

(71) Applicant: BEYOUNG SCIENTIFIC CO., LTD., Tainan (TW)

(72) Inventors: Chia-Ching Lee, Tainan (TW); Ming Hsiang Cheng, Taipei (TW)

(73) Assignee: BEYOUNG SCIENTIFIC CO., LTD., Tainan (TW)

( * ) Notice: Subject to any disclaimer, the term of this patent is extended or adjusted under 35 U.S.C. 154(b) by 48 days.

(21) Appl. No.: 16/285,397

(22) Filed: Feb. 26, 2019

(65) Prior Publication Data
US 2019/0307960 A1 Oct. 10, 2019

(30) Foreign Application Priority Data

Apr. 10, 2018 (TW) .................................. 107112234

(51) Int. Cl.
*A61M 5/30* (2006.01)
*A61M 5/20* (2006.01)

(52) U.S. Cl.
CPC ............ *A61M 5/30* (2013.01); *A61M 5/2033* (2013.01); *A61M 5/204* (2013.01); *A61M 2005/2073* (2013.01)

(58) Field of Classification Search
CPC ...... A61M 5/00; A61M 5/008; A61M 5/1452; A61M 5/14546; A61M 5/1456; A61M 5/14566; A61M 5/1458; A61M 5/178; A61M 5/20; A61M 5/28; A61M 5/281; A61M 5/30; A61M 5/31; A61M 2005/14573; A61M 2005/16863; A61M 2005/2073; A61M 2005/3139; A61M 2005/3142; A61M 2005/31588; A61M 2205/3584; A61M 2205/3492; A61M 2205/586; A61M 2205/8206; A61M 2205/8212; A61M 2209/04; A61M 2209/08; A61M 2209/082; A61M 2209/084

See application file for complete search history.

(56) References Cited

U.S. PATENT DOCUMENTS

| | | | | |
|---|---|---|---|---|
| 2,602,446 | A | * | 7/1952 | Glass .................. A61M 5/1452 604/155 |
| 2,702,547 | A | * | 2/1955 | Glass ................ A61M 5/14546 604/155 |
| 3,799,406 | A | * | 3/1974 | St. John ................ B01L 3/0234 222/309 |

(Continued)

*Primary Examiner* — Kami A Bosworth

(57) ABSTRACT

An automatic jet injector for administering tissue is provided with a housing including a grip and a pushbutton; a syringe positioning device on a top of the housing and including an intermediate support and a rear pushing board having a lower through hole and a threaded hole under the through hole; a power source in the housing and including a power supply configured to supply power to the power source by pressing the pushbutton; a fastening member in the housing and being adjacent to a rear end of the housing; a positioning member being adjacent to the power source; a reciprocating screw having a front end operatively connected to the power source and a rear end fastened in the fastening member; a rod having a front end fastened in the positioning member and a rear end fastened in the fastening member; and a control device.

10 Claims, 5 Drawing Sheets

(56) References Cited

U.S. PATENT DOCUMENTS

| | | | | |
|---|---|---|---|---|
| 3,858,581 | A * | 1/1975 | Kamen | A61M 5/1456 604/155 |
| 4,108,177 | A * | 8/1978 | Pistor | A61M 5/20 128/DIG. 1 |
| 4,191,187 | A * | 3/1980 | Wright | A61M 5/1456 604/155 |
| 4,424,720 | A * | 1/1984 | Bucchianeri | A61M 5/1456 128/DIG. 1 |
| 4,435,173 | A * | 3/1984 | Siposs | A61M 5/1456 128/DIG. 1 |
| 4,544,369 | A * | 10/1985 | Skakoon | A61M 5/1456 128/DIG. 12 |
| 4,804,368 | A * | 2/1989 | Skakoon | A61M 5/1456 128/DIG. 1 |
| 4,854,324 | A * | 8/1989 | Hirschman | A61M 5/14546 600/432 |
| 4,952,205 | A * | 8/1990 | Mauerer | A61M 5/1456 604/154 |
| 4,988,337 | A * | 1/1991 | Ito | A61M 5/1456 128/DIG. 12 |
| 5,034,003 | A * | 7/1991 | Denance | A61M 5/46 604/117 |
| 5,300,029 | A * | 4/1994 | Denance | A61M 5/20 128/DIG. 1 |
| 2002/0045861 | A1* | 4/2002 | Tribe | A61M 5/16831 604/154 |
| 2004/0006310 | A1* | 1/2004 | Geiser | A61M 5/1452 604/151 |
| 2005/0177111 | A1* | 8/2005 | Ozeri | A61M 5/1456 604/154 |
| 2005/0261633 | A1* | 11/2005 | Khalaj | A61M 5/20 604/181 |
| 2008/0281265 | A1* | 11/2008 | Hochman | A61M 5/158 604/110 |
| 2009/0188311 | A1* | 7/2009 | Cadieux | A61M 5/14546 73/149 |
| 2009/0299328 | A1* | 12/2009 | Mudd | A61M 5/31575 604/506 |
| 2010/0145263 | A1* | 6/2010 | Barak | A61M 5/1452 604/67 |
| 2011/0275410 | A1* | 11/2011 | Caffey | A61M 5/14593 455/557 |
| 2012/0065594 | A1* | 3/2012 | Scarborough | A61M 5/1456 604/218 |
| 2014/0131476 | A1* | 5/2014 | Kanetaka | H02N 2/14 239/102.1 |
| 2014/0221925 | A1* | 8/2014 | Kondoh | A61M 5/31568 604/111 |
| 2015/0265764 | A1* | 9/2015 | Weber | A61M 5/5086 604/111 |
| 2015/0289900 | A1* | 10/2015 | Asahi | A61M 3/02 606/167 |
| 2017/0333623 | A1* | 11/2017 | Kamen | G06F 19/3418 |
| 2018/0272068 | A1* | 9/2018 | Ko | A61B 1/00052 |
| 2018/0333527 | A1* | 11/2018 | Wen | A61M 1/1037 |
| 2019/0015576 | A1* | 1/2019 | Tan | A61M 1/28 |
| 2019/0224408 | A1* | 7/2019 | Thomas | A61M 5/1458 |
| 2019/0321837 | A1* | 10/2019 | Bhogal | B05B 7/2429 |

* cited by examiner

AUTOMATIC JET INJECTOR FOR ADMINISTERING TISSUE

BACKGROUND OF THE INVENTION

1. Field of the Invention

The invention relates to medical injection instruments and more particularly to an automatic jet injector for administering tissue, the jet injector adapted to allow a conventional syringe to mount thereon and being electrically activated, thereby rendering an administrating operation easy, quickly and saving labor.

2. Description of Related Art

In aesthetic medicine procedures, a surgeon may use a jet injector to facilitate surgery. A conventional hand operated jet injector 90 is shown in FIG. 5 and comprises a syringe (not shown) filled with tissue and mounted on a top, a grip 91, a trigger 92 extending downward, forward out of the grip 91, a dosage adjustment screw 93 operatively connected to the trigger 92, a cam type positioning member 94 attached to the dosage adjustment screw 93, a helical spring 95 interconnecting the trigger 92 and the cam type positioning member 94, a pushing mechanism 96 activated by the trigger 92, and a pushing board 97.

In an injection procedure, an operator may use one hand to press the trigger 92 toward the grip 91. In turn, the pushing mechanism 96 is activated to push the pushing board 97 forward. Further, a plunger of the syringe is pushed forward by the pushing board 97 to expel tissue through a discharge orifice at the front open end of the syringe.

However, the conventional hand operated jet injector 90 has the following disadvantages: complicated operations, being hand operated, not appropriate for long time operation, hurting the finger which often pushes the trigger 92, and a clogged dosage in the syringe may cause excessive dosage to expel into the body of an individual, resulting in an increase of surgery risk.

Thus, the need for improvement still exists.

SUMMARY OF THE INVENTION

It is therefore one object of the invention to provide an automatic jet injector for administering tissue, including a housing including a grip and a pushbutton projecting out of the grip, a syringe positioning device disposed on a top of the housing and including an intermediate support and a rear pushing board for pushing a syringe, the pushing board having at least one through hole on a lower portion, and a threaded hole under the through hole. A power source is disposed in the housing and a power supply is electrically connected to the power source wherein the power supply is configured to supply power to the power source by pressing the pushbutton. A fastening member is disposed in the housing and is adjacent to a rear end of the housing, a positioning member is disposed in the housing and is adjacent to a rear end of the power source. A reciprocating screw has a front end operatively connected to the power source after passing through the positioning member and a rear end fastened in the fastening member after passing through the threaded hole, at least one rod being parallel to the reciprocating screw, each of the at least one rod having a front end fastened in the positioning member and a rear end fastened in the fastening member after passing through the through hole. A control device is operatively connected to the power source and adapted to control a rotational speed of the power source, and a feedback module is adapted to detect whether the power source operates normally or not, wherein in case of the syringe being clogged by the tissue in the injection procedure, a warning signal indicating abnormality is generated by a circuitry of the power source and transmitted to a screen of the control device by the feedback module, and a corresponding message of the warning signal is shown on the screen to alert the operator to replace the malfunctioned syringe. In addition, the feedback module flashes a light or makes a buzzing sound to alert the operator to replace the malfunctioned syringe.

Preferably, the syringe positioning device includes a front threaded fastener for fastening a needle adapter of a syringe.

Preferably, at least one control button is provided on an outer surface of the housing and adapted to control a rotational direction of the power source.

Preferably, the power source is electrically connected to both the power supply and the pushbutton.

The invention has the following advantages and benefits in comparison with the conventional art: a correct, precise injection due to the electrically activated pushing board; the rod urging against the pushing board to convert a rotation of the reciprocating screw into a linear motion so that the pushing board may move stably; the control device adapted to set a rotational speed of the power source in quicker way in comparison with the conventional hand operated jet injector, thereby preventing the finger which often presses the trigger from being hurt; adjustable dosage administration; ergonomic grip; adapted to allow any of conventional syringes to mount thereon; and in case of the syringe being clogged by the tissue in the injection procedure, a warning signal indicating abnormality is generated by a circuitry of the power source, the warning signal is transmitted to a screen of the control device by the feedback module and a corresponding message "syringe replacement is required" of the warning signal is shown on the screen, thereby preventing excessive tissue from being injected into the body.

The above and other objects, features and advantages of the invention will become apparent from the following detailed description taken with the accompanying drawings.

DETAILED DESCRIPTION OF THE INVENTION

Figure 1:
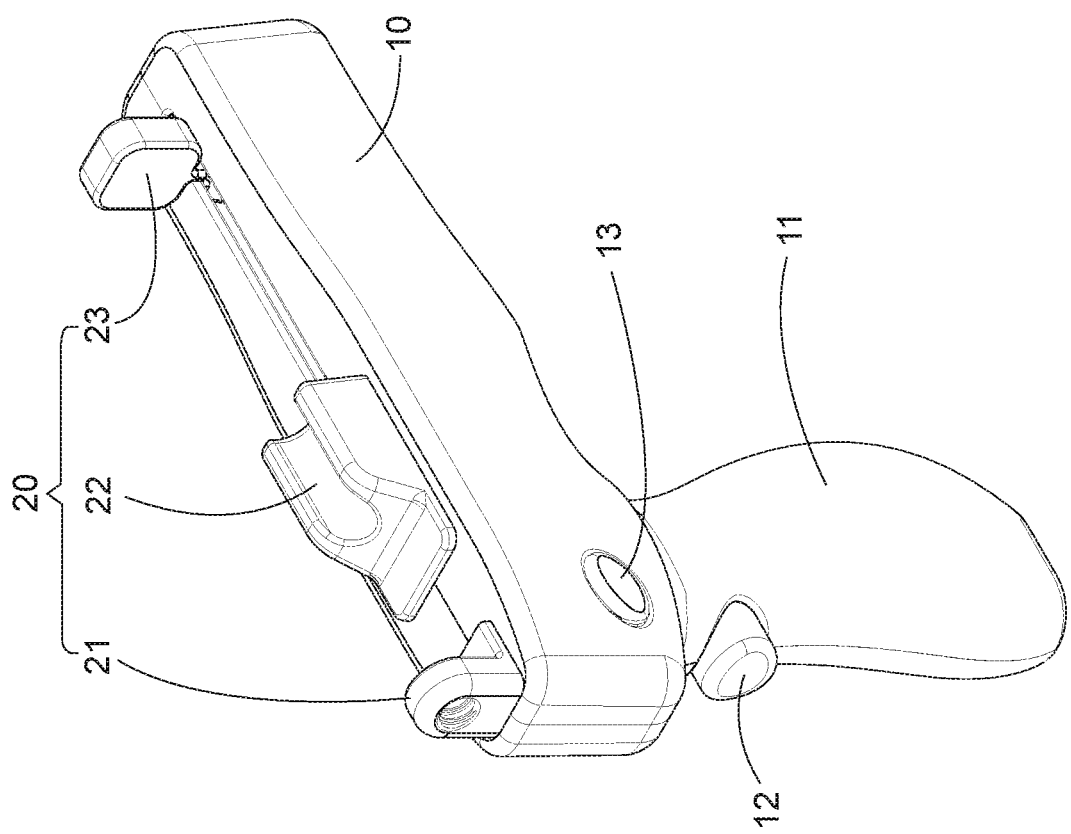
FIG. 1 is a perspective view of an automatic jet injector for administering tissue according to the invention.

Referring to FIGS. 1 to 4, an automatic jet injector for administering tissue in accordance with the invention includes the following components as discussed in detail below.

A housing 10 includes a downward extending grip 11 based on an ergonomic design, and a pushbutton 12.

A syringe positioning device 20 is disposed on a top of the housing 10 and includes an intermediate support 22, a front threaded fastener 21 for fastening a needle adapter of a syringe 100, and a rear pushing board 23 for pushing a plunger of the syringe 100, the pushing board 23 having at least one (one is shown) through hole 232 on a lower portion, and a threaded hole 233 under the through hole 232.

An internal fastening member 50 is disposed at a rear end of the housing 10.

A power source 30 is disposed in the housing 10 and adjacent to the grip 11. The power source 30 is electrically connected to the pushbutton 12 by wire. A power supply 31 is disposed in a compartment of the grip 11 and electrically connected to the power source 30. The power supply 31 may supply power to the power source 30 by pressing the pushbutton 12. A subsequent release of the pushbutton 12 may electrically disconnect the power supply 31 from the power source 30. The power source 30 can be a direct current (DC) motor, a step motor, a servo motor, a linear motor, a synchronous motor, an induction motor, or a reversible motor. The power supply 31 is implemented as cells or wires.

A positioning member 40 is disposed in the housing 10. The positioning member 40 and the housing 10 are either assembled or formed integrally. The positioning member 40 engages a rear end of the power source 30.

At least one rod (one is shown) 60 has a front end fastened in the positioning member 40 and a rear end fastened in the fastening member 50 after passing through the through hole 232.

A reciprocating screw 70 is parallel to the rod 60 and has a front end operatively connected to the power source 30 after passing through the positioning member 40 and a rear end fastened in the fastening member 50 after passing through the threaded hole 233. The threads of the reciprocating screw 70 mesh the threads of the threaded hole 233.

Alternatively, the threaded hole 233 is replaced by a hole having a nut like member (not shown) adapted to mesh the threads of the reciprocating screw 70. Preferably, the nut like member is formed of a material resistant to wear so that the reciprocating screw 70 can be used for a prolonged period of time.

The fastening member 50 is used to position both the rod 60 and the reciprocating screw 70 and keep a parallel relationship between them.

A control device 80 is operatively connected to the power source 30 and configured to control a rotational speed of the power source 30. Thus, the control device 80 can adjust a moving speed of the pushing board 23, thereby precisely controlling a dosage to be dispensed from the syringe 100.

Two control buttons 13 are disposed on two sides of the housing 10 respectively and electrically connected to the power source 30. One control button 13 is used to activate the pushing board 23 for injection and the other control button 13 is used to return the pushing board 23 to its default position after finishing the injection.

Figure 2:
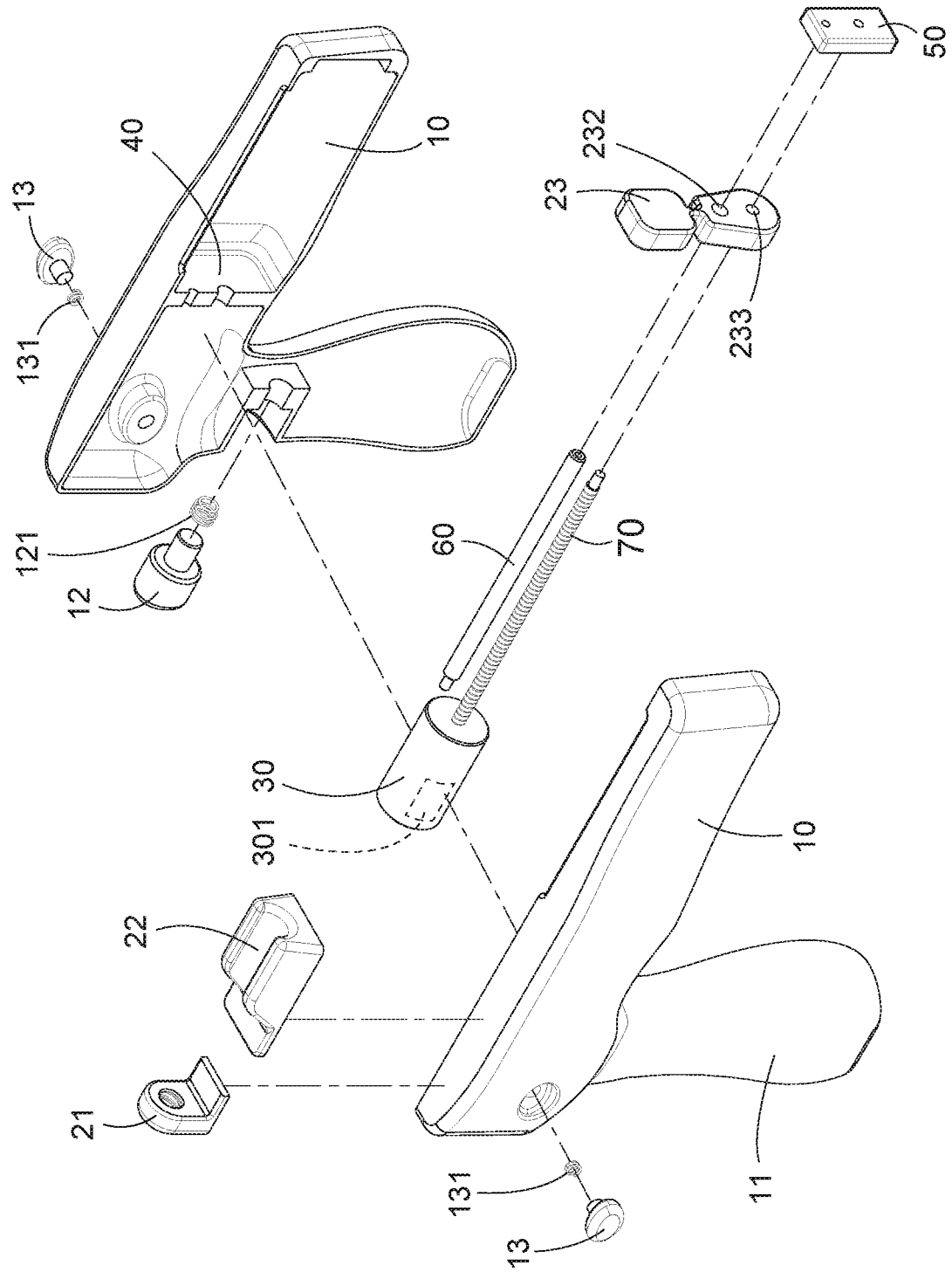
FIG. 2 is an exploded view of the automatic jet injector.

As shown in FIGS. 1 and 2 specifically, a first biasing member (e.g., torsion spring) 121 is put on a shaft of the pushbutton 12 and has two ends urging against the pushbutton 12 and the grip 11 respectively. As a result, the pushbutton 12 is a spring biased member, i.e., being capable of returning to its original position after being pressed. A second biasing member (e.g., torsion spring) 131 is put on a shaft of the control button 13 and has two ends urging against the control button 13 and the housing 10 respectively. As a result, each control button 13 is a spring biased member, i.e., being capable of returning to its original position after being pressed.

In the embodiment, each of the pushbutton 12 and the control buttons 13 is one of a plurality of control means such as toggle switch, electronic switch, and contact switch and both the pushbutton 12 and the control buttons 13 are used to activate the power source 30 or not and change a rotational direction of the power source 30.

Figure 3:
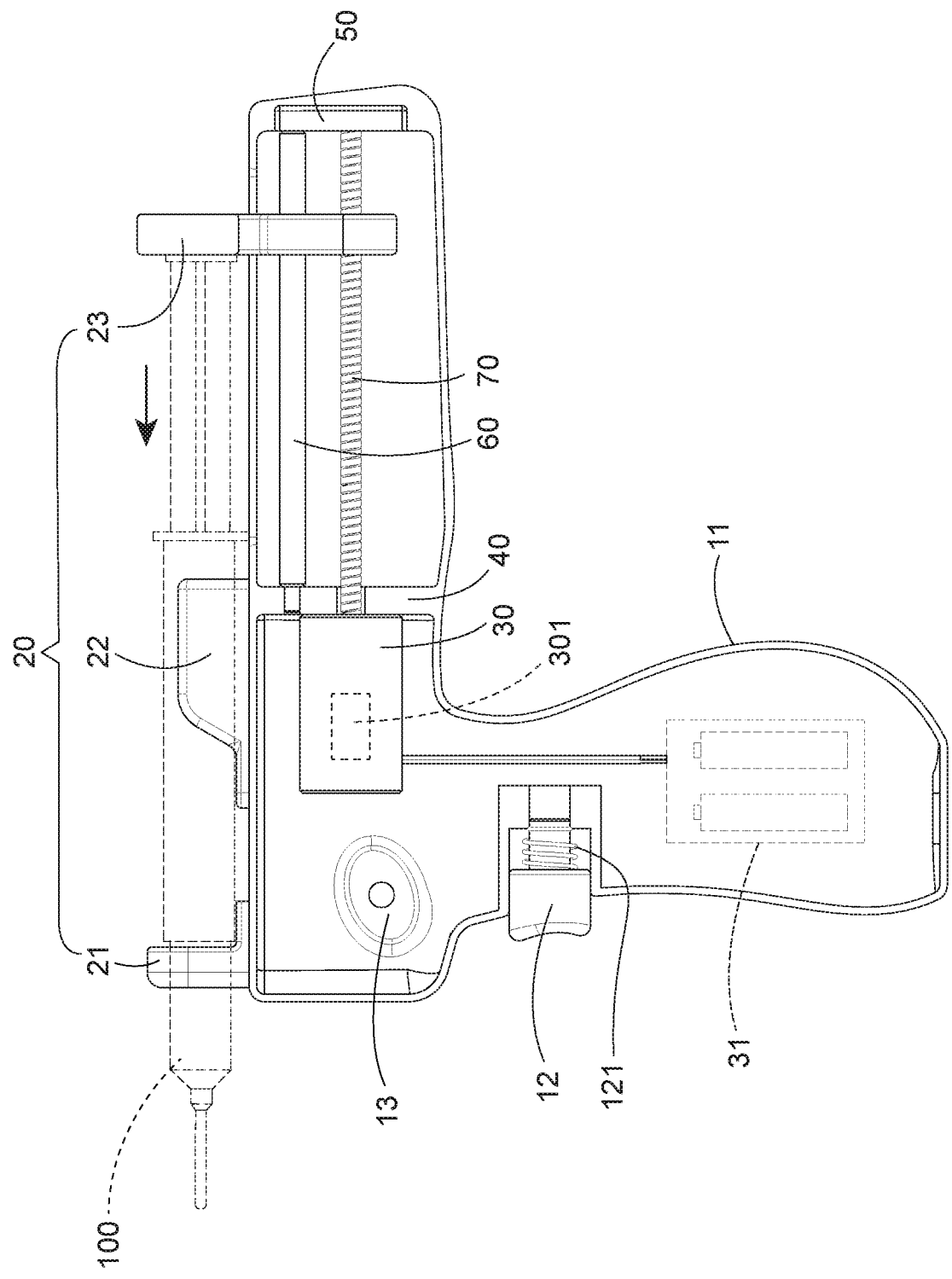
FIG. 3 is a schematic side elevation of the automatic jet injector.
Figure 4:
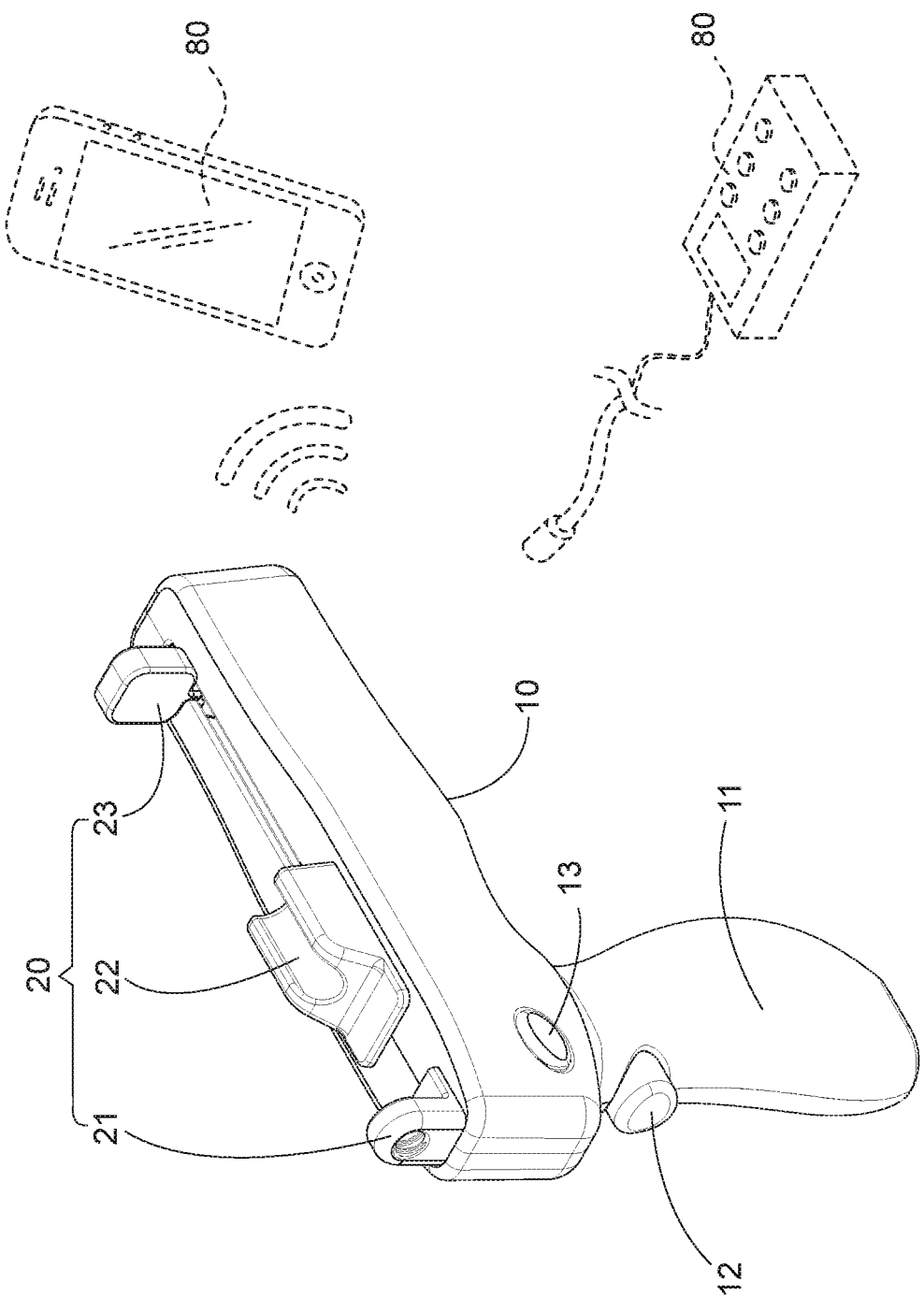
FIG. 4 is an environmental view showing an operation of the automatic jet injector.
Figure 5:
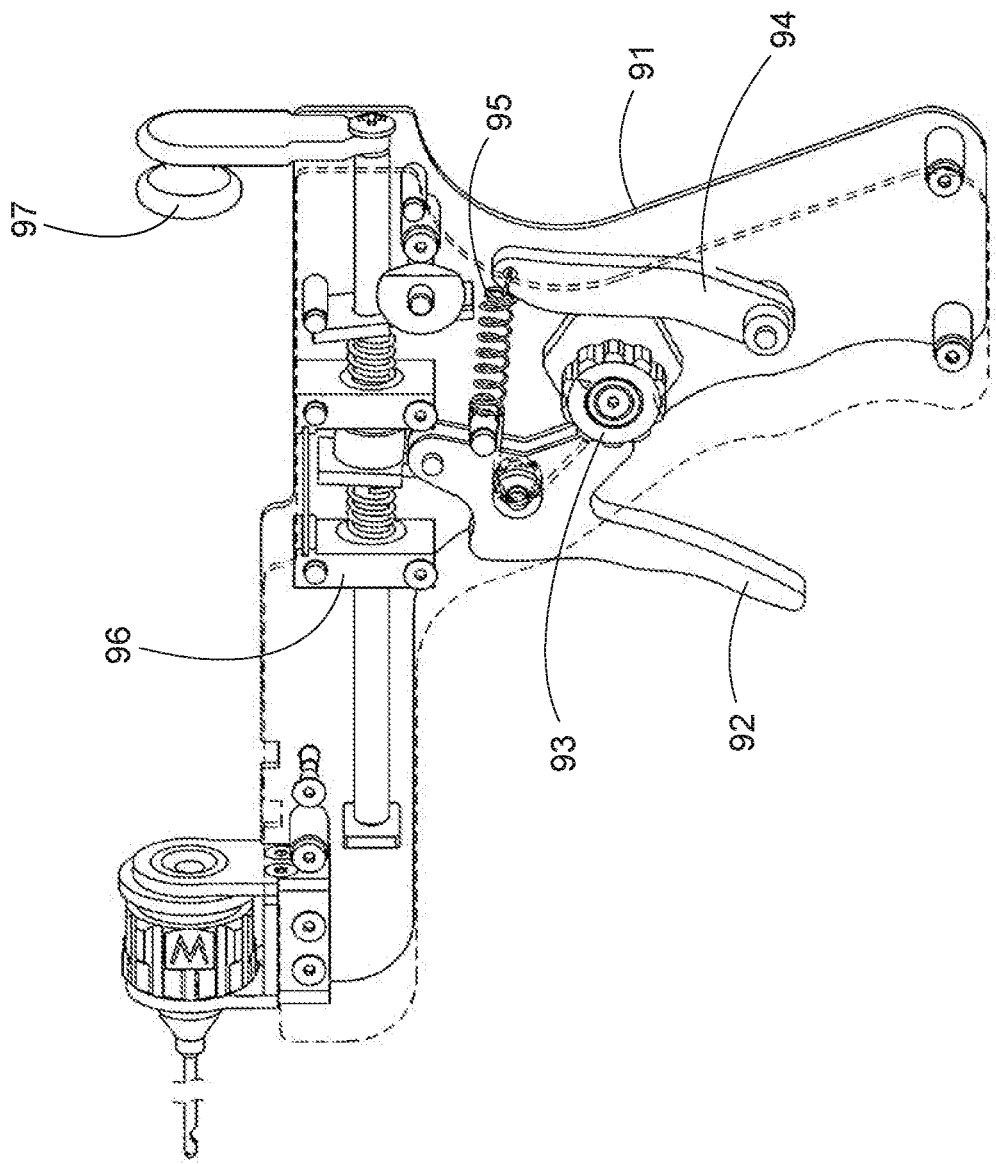
FIG. 5 is a schematic view of a conventional hand operated jet injector.

As shown in FIGS. 3 and 4 specifically, in the embodiment in an injection procedure, an operator may mount the syringe 100 filled with tissue on the syringe positioning device 20. Next, the operator may operate one of the control buttons 13 to ensure that the pushing board 23 urges against a rear end of the syringe 100. Next, the operator may press the pushbutton 12 to cause the pushing board 23 to push the syringe 100 forward. As a result, tissue in the syringe 100 is expelled through a discharge orifice at the front open end of the syringe 100 to inject into body issues. After the injection procedure, the operator may press the other control button 13 to counterclockwise rotate the power source 30. As a result, the pushing board 23 returns to its default position.

The invention is applicable to many different medical injections. For example, the tissue may be replaced with liquid. The syringe 100 of the invention has an integral hypodermic needle or a separate hypodermic needle that is connected to the syringe 100 as long as the syringe 100 is capable of being mounted between the front threaded fastener 21 and the rear pushing board 23.

The control device 80 is connected to the power source 30 either by wire or wirelessly so as to control the power source 30. In a wire implementation, a control key of the control device 80 is adapted to press to control a rotational speed of the power source 30. To the contrary, in a wireless implementation, a wireless transmission such as network, Bluetooth®, and infrared radiation of a smart device is used, and a mobile application (APP) of the smart device is used to control a rotational speed of the power source 30.

A feedback module 301 is used to detect whether the power source 30 operates normally. In case of the syringe 100 being clogged by the tissue in the injection procedure, a warning signal indicating abnormality is generated by a circuitry of the power source 30. The warning signal may indicate over current, over voltage or over power. Further, the warning signal is transmitted to a screen of the control device 80 by the feedback module 301 and a corresponding message of the warning signal is shown on the screen. For example, the message may show "syringe replacement is required". In addition, the feedback module 301 may flash a light or make a buzzing sound to alert the operator to replace the malfunctioned syringe 100.

The automatic jet injector for administering tissue of the invention has the following characteristics and advantages: a correct, precise injection, adjustable dosage administration, and preventing the finger which often pushes the pushbutton from being hurt.

While the invention has been described in terms of preferred embodiments, those skilled in the art will recognize that the invention can be practiced with modifications within the spirit and scope of the appended claims.

What is claimed is:

1. An automatic jet injector for administering tissue, comprising:
   a housing including a grip and a pushbutton projecting out of the grip;
   a syringe positioning device disposed on a top of the housing and including an intermediate support, a front fastener for fastening a syringe, the front fastener disposed at a front end of the housing, and a rear pushing board for pushing the syringe, the rear pushing board disposed at a rear end of the housing opposite the front end, and the rear pushing board having at least one through hole on a lower portion, and a threaded hole under the through hole,
wherein the front fastener has a threaded circular hole configured to receive the syringe;
a power source disposed in the housing and including a power supply electrically connected to the power source wherein the power supply is configured to supply power to the power source by pressing the pushbutton;
a fastening member disposed in the housing and being adjacent to the rear end of the housing;
a positioning member disposed in the housing and being adjacent to a rear end of the power source;
a reciprocating screw having a front end operatively connected to the power source after passing through the positioning member and a rear end fastened in the fastening member after passing through the threaded hole of the rear pushing board;
at least one rod being parallel to the reciprocating screw, each of the at least one rod having a front end fastened in the positioning member and a rear end fastened in the fastening member after passing through the at least one through hole; and
a control device operatively connected to the power source.

2. The automatic jet injector of claim 1, further comprising at least one control button on the housing configured to control a rotational direction of the power source.

3. The automatic jet injector of claim 1, wherein the power source is electrically connected to both the power supply and the pushbutton; and wherein the power source is a direct current (DC) motor, a step motor, a servo motor, a linear motor, a synchronous motor, an induction motor, or a reversible motor.

4. The automatic jet injector of claim 1, wherein the power supply is disposed in the grip and implemented as cells or wires.

5. The automatic jet injector of claim 1, wherein the control device includes a control key adapted to be pressed to control a rotational speed of the power source by transmitting a signal to the power source.

6. The automatic jet injector of claim 1, wherein the control device is configured to use network, Bluetooth®, or infrared radiation of a smart device, and use a mobile application of the smart device to control a rotational speed of the power source.

7. The automatic jet injector of claim 1, further comprising a feedback module in the power source for detecting whether the power source operates normally, wherein a signal indicating an abnormality is generated when an over current, over voltage or over power event occurs, the signal being adapted to issue a warning by means of a message, flashing a light or making a buzzing sound.

8. The automatic jet injector of claim 1, wherein the positioning member is formed integrally in the housing.

9. The automatic jet injector of claim 1, wherein the positioning member is disposed in the housing by assembly.

10. The automatic jet injector of claim 1, wherein threads of the reciprocating screw mesh threads of the threaded hole of the rear pushing board.

* * * * *